United States Patent [19]

Prugnaud

[11] 4,071,314

[45] Jan. 31, 1978

[54] PROCESSES, REAGENTS AND MEANS FOR EARLY DIAGNOSIS OF PREGNANCY

[75] Inventor: Robert Louis Prugnaud, Paris, France

[73] Assignee: Laboratoire Theranol, Paris, France

[21] Appl. No.: 701,034

[22] Filed: June 29, 1976

Related U.S. Application Data

[63] Continuation-in-part of Ser. No. 430,935, Jan. 4, 1974, abandoned.

[30] Foreign Application Priority Data

Jan. 8, 1973  France .................................. 73.00496

[51] Int. Cl.² ...................... G01N 33/16; A61K 37/38
[52] U.S. Cl. ...................................... 23/230 B; 424/12
[58] Field of Search ...................... 23/230 B, 253 TP; 424/12

[56] References Cited

U.S. PATENT DOCUMENTS

| 3,234,096 | 2/1966 | Pollack | 424/2 X |
|---|---|---|---|
| 3,309,275 | 3/1967 | Treacy | 424/2 X |
| 3,579,306 | 5/1971 | Crane | 424/12 X |

FOREIGN PATENT DOCUMENTS

| 1,299,171 | 6/1962 | France. | |
| 1,322,869 | 2/1963 | France. | |
| 1,343,189 | 10/1963 | France. | |
| 1,411,279 | 8/1965 | France. | |
| 979,759 | 1/1965 | United Kingdom | 424/12 |
| 1,155,365 | 6/1969 | United Kingdom | 424/12 |

OTHER PUBLICATIONS

Gradwohl, "Clinical Laboratory Methods and Diagnosis," C. V. Mosby Co., St. Louis, 1970, pp. 1576, 1577, 1579–1584.

Todd–Sanford, "Clinical Diagnosis by Laboratory Methods," 14 ed., W. B. Saunders Co., Philadelphia, Pa., 1969, pp. 1181–1187.

Kerber, et al., "Immunologic Tests for Pregnancy," Obstetrics and Gynecology, vol. 36, No. 1, July 1970.

*Primary Examiner*—Joseph Scovronek
*Assistant Examiner*—Arnold Turk
*Attorney, Agent, or Firm*—Browdy and Neimark

[57] ABSTRACT

A reagent for the early diagnosis of pregnancy comprising a substrate of suitable erythrocytes or polymer having adsorbed thereon a predetermined ratio of chorionic gonadotropin antigen and antisera therefor. The ratio is selected so as to be insensitive to the presence of less than 1,500 I.U. per liter of chorionic gonadotropin in the urine being tested. The reagent is used by combining with a predetermined quantity of the urine to be tested and after ½–2 hours inspecting for agglutination, the presence of which indicates a negative result. An apparatus is also disclosed for carrying out the process.

9 Claims, 1 Drawing Figure

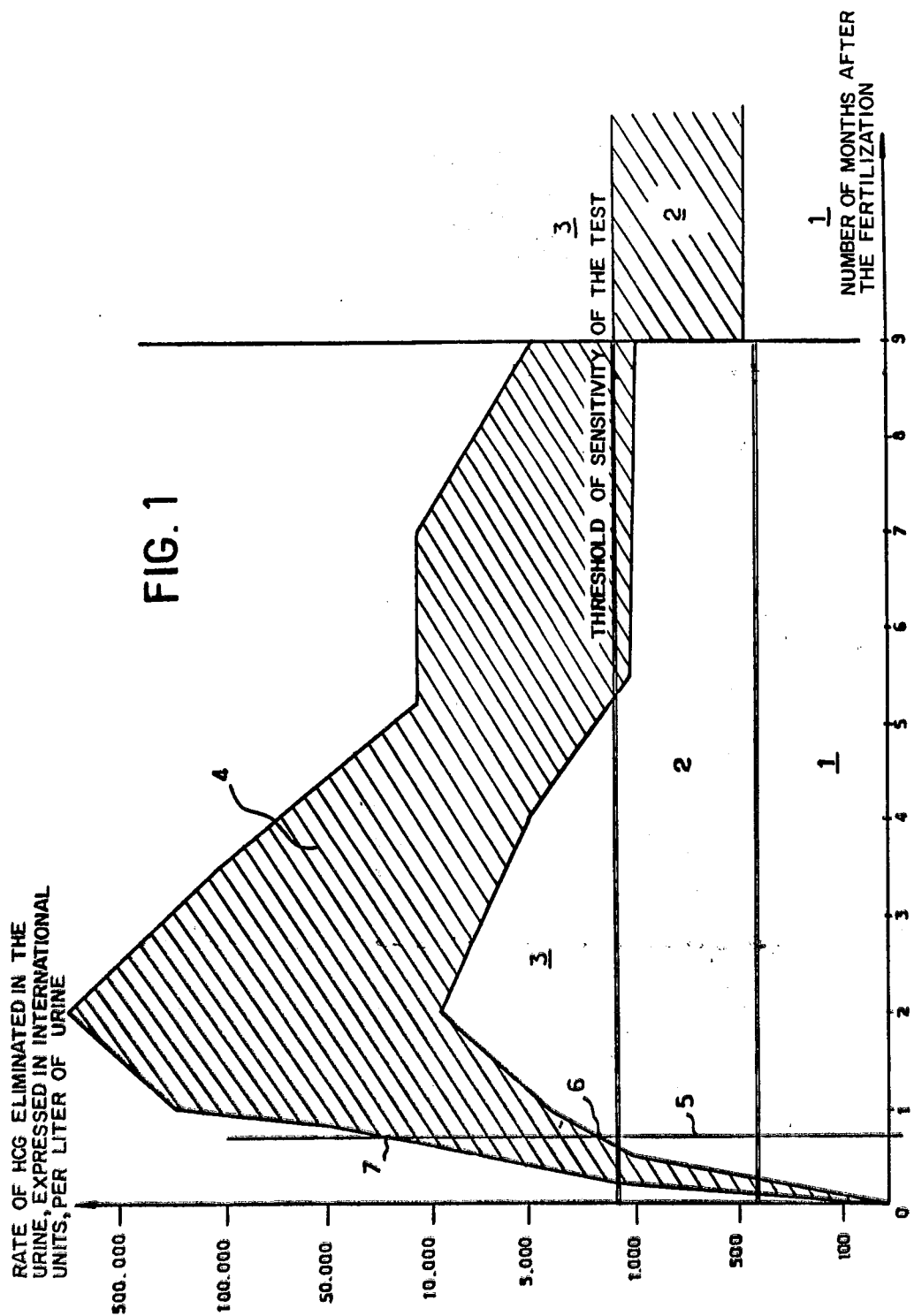

PROCESSES, REAGENTS AND MEANS FOR EARLY DIAGNOSIS OF PREGNANCY

This is a continuation-in-part application of copending application Ser. No. 430,935 filed Jan. 4, 1974, now abandoned, which is hereby incorporated by reference, which application has now been withdrawn in favor of the present application.

FIELD OF THE INVENTION

The present invention relates to a new and novel process for an early diagnosis of pregnancy and further to a modified reagent and improved means for implementing the process.

BACKGROUND OF THE INVENTION

As is known, the gonadotropic hormones or gonadotropins are hormones stimulating the gonads. In mammals, the gonadotropins are generated by the hypophysis, the placenta, and, as regards pregnant mares, also by the endometrium. The gonadotropic hormones comprise the follicle-stimulating ones (FSH), the luteinizing ones (LH) luteotropine (LTH) and chorionic gonadotropin (HCG). It is known that the biological effects of HCG and LH are similar. It is also known that the urine of pregnant mammals contains chorionic gonadotropin of placental origin and that in women, in the midst of the menstrual cycle, the urine contains LH of hypophyseal origin of which the action causes ovulation and formation of yellow body. It is further known that the urine of the female in the pre-menopause period, that is, in the case of incipient menopause, contains gonadotropins of hypophyseal origin.

The presence of chorionic gonadotropin of placental origin in the urine constitutes one of the early diagnostic means for pregnancy. This is the reason reagents allowing early diagnosis of pregnancy were developed.

These reagents in essence are substrates on which are adsorbed antigens consisting of chorionic gonadotropins (HCG) and chorionic gonadotropin antisera; the reaction between the HCG antigen and the antiserum on the substrate results in a clear, yellow precipitate homogeneous in nature, i.e. the agglutinate. When there is excess of free HCG in the reactive medium — for instance when the HCG is obtained from the urine of the pregnant female — there will be no reaction as above, it being inhibited by the presence of HCG in the urine, and no agglutinate will be formed.

When the substrate on which the HCG is adsorbed consists of suitably treated erythrocytes and when there is no erythrocyte-antiserum reaction, and no agglutinate is formed, the erythrocytes will settle at the bottom of the test tube as a dark-brown ring. This reaction, which is known as the WIDE & GEMZELL reaction, was described in ACTA ENDOCRINOL, 35, 261 (1960); it was applied in French Pat. Nos. 1,299,171 and 1,343,189 under the name of ORGANON N.V. Also please see French Pat. No. 1,516,630 (U.S. equivalent U.S. Pat. No. 3,548,051) and French Pat. No. 1,186,147.

When the substrate used consists of a synthetic polymer as described in French Pat. Nos. 1,322,869 and 1,411,279 under the name of ORTHO PHARMACEUTICAL CORP., wherein the antigen/antiserum reaction is inhibited by the presence of HCG in the urine being tested, there will be no agglutination reaction.

However, the reagents described in the patents above are so sensitive that the antigen/antiserum reaction will be inhibited not only when the urine being tested contains chorionic gonadotropin from a pregnant subject, that is, of placental origin, but also when such urine contains gonadotropins of hypophyseal origin as in the cases of incipient menopause and in the middle of the menstrual cycle.

SUMMARY OF THE INVENTION

It has now been found that the gonadotropins of hypophyseal origin will be eliminated in the urine both for incipient menopause and for the middle of a menstrual cycle in proportions always less than 500 I.U. per liter of urine.

On the other hand, if a quantitative and early test for pregnancy is undertaken the 9th day of delay in menstruation, then, as shown by experiment, the elimination rate of the chorionic gonadotropins (HCG) in the urine will always exceed 1,500 I.U. per liter of urine if there is pregnancy.

The intermediate zone between the HCG elimination rates of 500 and 1,500 I.U. per liter of urine lends itself to no useful interpretation since the rates falling within this zone are larger than those of incipient menopause and of the middles of the menstrual cycles, while less than those allowing diagnosis of a normal pregnancy. The present invention requires that the reagent used for indicating early pregnancy be of sufficiently high threshold to eliminate any chance of error or confusion, so that absence of agglutination occurs and is observed only when chorionic gonadotropin is present in the urine of a pregnant female.

In other words, the sensitivity threshold of the present invention must exceed 1,500 I.U. of HCG per liter of urine being examined.

The necessity for a reaction threshold exceeding 1,500 I.U. of HCG eliminated per liter of urine will become clear when examining attached FIG. 1 showing a graph of HCG elimination during pregnancy, showing as abscissa the number of months between fertilization (0) and delivery (9), and as ordinate the rate of the HCG eliminated in the urine and expressed in I.U. of HCG plotted on a logarithmic scale.

In this graph, zone 1 shows the region of elimination of the gonadotropin of hypophyseal origin eliminated in the urine for the case of incipient menopause and for the middle of the menstrual cycle, essentially covering the range of 0 to 500 I.U. of HCG/liter of urine. Region 2 corresponds to the intermediate range essentially comprising 500 to 1,500 I.U. of HCG/liter of urine elimination. An uneven reaction takes place and a more or less pronounced ring is likely to occur when the substrate being used consists of erythrocytes. Accordingly, the test undertaken in such instances is not amenable to results allowing clear interpretation. Zone 3 corresponds to the HCG elimination rates expressed as I.U. per liter of urine during pregnancy, during which there is no agglutination, so that the reaction medium will be appreciably clear. When erythrocytes are used as the substrate they will deposit at the bottom of such medium.

Shaded zone 4 corresponds to a sketch of the elimination of the HCG during pregnancy from fertilization to birth. The straight line 5 which is parallel to the ordinate shows the optimum date for the earliest performance possible of the diagnostic test, that is, the ninth day following delay in menstruation. Point 6 formed by the intersection of the straight line 5 with the lower boundary of zone 4, and point 7 formed by the intersection of straight line 5 with the upper boundary of zone 4, respectively show the minimum and maximum elimination rates of HCG per liter of urine on the 9th day of delay in menstruation.

The object of the present invention therefore is to create a process, a reagent and means allowing early diagnosis of pregnancy, which will better satisfy practical requirements than known processes and means with the same purpose, said object being achieved in particular by the process, reagents and means of the invention, allowing a practical and reliable early diagnosis from which are eliminated any possible influences due to incipient menopause and middles of perturbed menstrual cycles. Furthermore, the present invention allows execution of the process and use of the reagents and the means by personnel not trained in hormonology and immunology. Reading of the reactions is practical, specific and reliable, the urine being tested in such manner that virtually any ambiguity will be eliminated in interpreting the presence of pregnancy in the person under consideration.

The object of the present invention is a process for early pregnancy diagnosis in mammals in which pregnancy causes the elimination of chorionic gonadotropin of placental origin in the urine, particularly as regards the human female, making use of a multi-component reagent including a first substance essentially comprising a substrate which may consist of suitably treated erythrocytes or of a synthetic polymer on which is adsorbed chorionic gonadotropin endowed with antigen properties, and a second substance acting as antiserum with respect to this hormone. The process is characterized in that the possibly diluted urine is made to react in a reaction medium with such two substances as described above and so modified as to be wholly insensitive to chorionic gonadotropin when the latter is eliminated in the urine until the rate exceeds 1,500 I.U. of HCG per liter of urine. The reactive mixture is allowed to stand from half an hour to 2 hours, after which time examination will take place regarding presence of agglutination, or regarding whether the latter was inhibited by the presence of any chorionic gonadotropin due to pregnancy. Proof of such inhibition is found by the deposition of a ring of erythrocytes if latter were used as substrates for the antigenic HCG.

Another object of the present invention is a multi-component reagent for early diagnosis of pregnancy, including a first substance essentially comprising a substrate constituted, for instance, of erthrocytes or of synthetic polymers on which is adsorbed chorionic gonadotropin, associated with a second substance acting as an antiserum with respect to the latter hormone. This reagent is characterized by being so modified as to provide in the mixed liquid state with urine a selective sensitivity threshold with respect to the chorionic gonadotropin eliminated in the urine which will be higher than 1,500 I.U. of HCG per liter of urine.

For a better understanding of the invention possible embodiments thereof will now be described, it being understood that such embodiments are intended as merely exemplary and in no way limitative.

BRIEF DESCRIPTION OF THE DRAWING

FIG. 1 is a graph showing the quantity of HCG elimination during pregnancy.

DESCRIPTION OF PREFERRED EMBODIMENTS

In one advantageous embodiment for the reagent of this invention, the ratio of the antibody concentration in the antiserum/antigen of the reagent is computed in such manner that the agglutination reaction will be entirely inhibited beyond a rate of 1,500 I.U. of HCG per liter of urine.

In another preferred embodiment of the reagent, the antibody concentration of the antiserum is varied by increasing the volume of the antiserum.

In another preferred embodiment of this reagent, the antisera will be selected from the rabbits' supplies of which the antibody concentration is highest.

In another advantageous embodiment of the invention relating to the reagent, the denominator of the antibody concentration ratio of antiserum/antigen will be varied, i.e. the amount of antigen will be changed, by varying the amount of substrate adsorbing the antigen.

In another embodiment of the invention, the amount of antigen adsorbed on the substrate may be varied.

The multi-component reagent is prepared in accordance with a preferred mode of placing a suspension of the HCG adsorbed substrate (antigen) in a saline isotonic solution in a tube in which the suspension is frozen. A buffer solution containing EDTA is then added to the tube above the frozen quantity of antigen, and the buffer is also frozen. Next, the antiserum solution is added to the tube and this solution is frozen. The three layers of frozen material are then lyophilized, the EDTA - buffer composition serving to separate the superimposed antigen and anti-serum layers in order to hinder an untimely reaction between the antigen and the antiserum.

The key feature which must be utilized in order to obtain the advantages of the present invention is that the quantities of antigen and of antiserum present in the liquid reaction medium must be calculated in order to obtain a positive reaction to the presence of 1,500 IU of HCG per liter and a negative reaction at or under 1,000 IU of HCG per liter.

To accomplish this type of control, the components of the multi-component reagent are selected, in one preferred embodiment, as follows:

The antigen (e.g. erythrocyte) component layer: This component, constituting the bottom lyophilized layer of the dried components, comprises 0.36–0.44 ml of a 4% suspension of sheep erythrocytes on which is adsorbed formol-sensibilized HCG, the suspension weighing, after lyophilization, about 16 ml.

The buffer layer: The buffer layer is utilized, in the reaction medium to adjust the pH. The buffer comprises a mixture of disodium phosphate and potassium acid phosphate to which is added ethylene diamine tetracetic acid (EDTA) as a chelating agent, the preferred quantities being 0.495 mg disodium phosphate; 0.072 mg potassium acid phosphate; and 0.40 mg of the sodium salt of EDTA per tube of reagent. The above-mentioned EDTA content is in excess in order to thoroughly complex the calcium ions eventually present in the urine. Such buffer solution is added in each tube as a solution in a quantity of 0.1 to 0.2 ml.

The anti-serum component layer: This layer, the upper layer of lyophilized material in the tube, comprises 0.36–0.44 ml of serum taken from rabbits which were injected with HCG, and this corresponds to about 7–8 ml of dry extract per tube.

Whereas in the prior art the EDTA was used as a separate solution, in accordance with the present invention the EDTA is added to the phosphate buffer. The provision of the EDTA in the buffer, and also the modification involving the use of an excess quantity of EDTA, provided for a better visualization of the pregnancy testing reaction.

The general proportions of the top and bottom layers which in particular give the desired results of obtaining a positive reaction in the presence of 1,500 IU of HCG per liter and a negative reaction at or under 1,000 IU of HCG per liter, are as follows: If the tube contents are for instance three hundred million erythrocytes, the ratio of erythrocytes to anti-serum is 300 million/200 thousand to 250 thousand, and this corresponds, for instance, to a quantity of anti-serum, expressed in dry extract, of 6,600 to 7,500 micrograms. Thus, each tube will contain (wet basis) approximately 0.20–0.44 ml of an approximately 3–6% suspension of erythrocytes, preferably 0.36–0.44 ml of a 4% suspension, sensibilized to HCG, as one dry layer. Separated therefrom by the buffer layer will be (wet basis) approximately 0.30–0.60 ml, preferably 0.36–0.44 ml, of the dried anti-serum solution.

Thus, with these reciprocal contents of antigen and anti-serum, a positive reaction is obtained when the components are mixed together in the presence of urine containing 1,500 IU of HCG or more per liter of urine, and a negative reaction occurs only at or under 1,000 IU of HCG per liter of urine.

In accordance with a preferred process of the present invention for the early diagnosis of pregnancy in mammals for whom pregnancy causes the excretion of chorionic gonadotropin of placental origin in the urine, and in particular in the case of women, with the use of a reagent which comprises a support essentially made of erythrocytes or a synthetic polymer on which is adsorbed the chorionic gonadotropin, which is endowed with antigen properties, and an anti-serum with respect to this hormone, the following steps are carried out:

— contacting the urine to be examined, in a possibly diluted state, with a reagent of the above type presenting a threshold of selective sensitivity with respect to the chorionic gonadotropin excreted in the urine, i.e., greater than 1,500 IU of HCG/liter of urine, by introducing such urine into the reagent comprising the support and the antiserum in a ratio which is in the order of $3 \times 10^8 / 2 \times 10^5$ to $2.5 \times 10^5$, which corresponds to a quantity of anti-serum, expressed as dry extract, which on the order of about 6,600–7,500 micrograms for $3 \times 10^8$ erythrocytes, such reagent having been prepared by lyophilization, by separating the respective layers of erythrocytes and anti-serum by interposition therebetween of a buffer composition consisting essentially of a phosphate buffer together with ethylene diamine tetracetic acid which acts as a chelating agent with respect to the calcium ions possibly present in the urine;

— leaving the reaction mixture to rest for ½ to 2 hours;

— and then examining the reaction mixture to see if the agglutination reaction has taken place or if it has been inhibited by the possible presence of pregnant chorionic gonadotropin in the urine tested, the inhibition having been proven by the deposit of a ring formed by the support.

The reagent for early diagnosis of pregnancy used in the preferred process mentioned above consists essentially of a support of erythrocytes or synthetic resin, on which is adsorbed the chorionic gonadotropin, the support being associated with an anti-serum of the hormone, the reagent being characterized in that it presents a threshold of selective sensitivity with respect to the chorionic gonadotropin excreted in the urine which is greater than 1,500 IU of HCG/liter of urine. The ratio of the support to the anti-serum is on the order of $3 \times 10^8 / 2 \times 10^5$ to $2.5 \times 10^5$, which corresponds to a quantity of anti-serum, expressed as dry extract, on the order of about 6,600–7,500 micrograms for $3 \times 10^8$ erythrocytes, the multi-component reagent having been prepared by lyophilization with the layers of support and anti-serum separated by interposition therebetween of a phosphate buffer composition layer containing ethylene diamine tetracetic acid which exercises a chelating activity with respect to calcium ions possibly present in the urine.

In conformity with an advantageous embodiment of the apparatus of the present invention, the tube or similar device holds the multi-component reagent which is so modified that when the urine being examined holds less than 1,500 I.U. of HCG per liter, it will cause an erythrocyte/antibody agglutination in the form of a clear precipitate of homogeneous nature, and when the urine examined contains more than 1,500 I.U. of HCG per liter, the agglutination reaction will not occur, and when the antigen substrate consists of erythrocytes, these will deposit as a ring, having failed to react with the antibodies in view of the inhibiting action of the HCG in the urine being examined.

A preferred embodiment of the apparatus of the invention consists in associating reference images of the likely two kinds of reactions with the mirror reflecting the image of the bottom of the tube where the diagnosing reaction takes place. The reference images are used as comparison standards with the actual one obtained by the mirror and reflected from it.

Another embodiment of the apparatus of the present invention consists in associating image-fixing means for the image obtained from the reaction tube, for instance a sensitive plate or similar device, with said apparatus.

In addition to provisions described above, the invention also includes other arrangements associated with the following description.

The present invention especially applies to the processes, reagents and implementation means of early pregnancy diagnosis that are in conformity with the arrangements described above, and furthermore relates to any agent, arrangement, apparatus, design etc. that are suitable for implementing such process and for embodying these reagents and means.

Operation of the invention is as follows:

Having collected the first urine of the day (possibly storing it in a sealed bottle away from heat), the diagnostician or the woman herself takes a predetermined quantity of drops by means of a dropper and introduces them into the tube which contains the dried, three layer reagent; then the diluting liquid is introduced — which advantageously may be distilled water — from a second container or the like.

After sealing the reagent tube and shaking same well, it is put back on a support and let to rest on a plane surface, free from any vibration and heat, avoiding any handling in the course of the subsequent 2 hours of standing; the same care must be exerted at the end of the 2 hour interval. The diagnostician or the woman will then inspect the bottom of the tube.

If the image of the tube bottom is solid brown-yellow liquid, then there was an agglutination reaction, and therefore the test is negative and there is no pregnancy.

If the image of the tube bottom is either urine of unchanged color and turbidity (which would be the case of the substrate of the antigen HCG being made of a synthetic polymer), or else a regular, dark-brown ring of variable dimensions (this is the case of the antigen HCG substrate consisting of erythrocytes), then the agglutination reaction was inhibited by the presence of chorionic gonadotropin in the tested urine; the test is positive and there is pregnancy.

It follows from the above description that regardless of the implementing means, or of the embodiments and particular modes, a new and novel process and a modified reagent will be obtained for early pregnancy diagnosis. Furthermore, new means for implementing this process and utilizing this reagent are provided, which, with respect to previously known processes, reagents and means, offer significant advantages that were clearly described above and which further advantageously allow extending their applications without requiring adaptation. For example, they allow easy and rapid detection of chorionic gonadotropin in the urine of males afflicted with testicular tumors of the teratoma and epithelioma types.

As shown by the above, the invention will in no manner be limited to the embodiment modes, to the implementation and application that were described in explicit manner; on the contrary, it covers all variations that may occur to the expert in the matter without thereby leaving the domain or significance of the present invention.

What is claimed is:

1. In a process for early diagnosis of pregnancy in mammals for whom pregnancy causes elimination of chorionic gonadotropin of placental origin in the urine comprising:

combining a predetermined quantity and dilution of urine from a subject being tested for pregnancy with a reagent comprising a storable, dry composition mixable with diluting liquid immediately prior to usage, said composition comprising a substrate of erythrocytes or synthetic polymer suitable for use as such a substrate on which are adsorbed chorionic gonadotropin endowed with antigen properties and said composition including a substance acting as an anti-serum with respect to this antigen;

allowing the mixture to stand from one-half to 2 hours; and inspecting the mixture for the occurrence of agglutination reaction or the inhibition thereof, the improvement wherein the ratio of said adsorbed chorionic gonadotropin endowed with antigen properties to said substance acting as an anti-serum with respect to this hormone is such that said reagent is sensitive to chorionic gonadotropin in the urine only when the latter is eliminated in the urine at a rate exceeding 1,500 I.U. of chorionic gonadotropin per liter of urine, and the agglutination reaction is prevented when the urine contains more than 1,500 I.U. of chorionic gonadotropin per liter of urine.

and wherein said composition comprises three superimposed dried layers, the lower layer comprising said substrate having adsorbed thereon said HCG antigen, the top layer comprising said antiserum, and a middle layer interposed between said bottom and top layers, said middle layer comprising a phosphate buffer containing a calcium ion chelating agent.

2. A process in accordance with claim 1, wherein said urine from the subject being tested is urine taken the nineth day of delay in menstruation.

3. In a reagent for early pregnancy diagnosis, said reagent consisting essentially of a diluting liquid and a storable, dry composition of a substrate consisting essentially of erythrocytes or of synthetic polymer suitable for use as such a substrate, said substrate having adsorbed thereon chorionic gonadotropin (HCG) antigen and said composition including a substance acting as an antiserum with respect to said antigen, the improvement comprising:

means to positively show pregnancy only when the rate of HCG exceeds 1,500 I.U. per liter of urine, said means comprising said reagent wherein the ratio of antigen to antiserum is selected so as to endow said reagent with a selective sensitivity threshold as regards to amount of chorionic gonadotropin eliminated in the urine so that said reagent will provide agglutination which is a negative pregnancy reaction when mixed with urine only when such urine contains less than 1,500 I.U. of HCG per liter of urine, said reagent being wholly insensitive of chorionic gonadotropin when the latter is eliminated in the urine until the rate exceeds 1,500 I.U. of HCG per liter of urine and wherein said reagent comprises three superimposed dried layers, the lower layer comprising said substrate having adsorbed thereon said HCG antigen, the top layer comprising said antiserum, and a middle layer interposed between said bottom and top layers, said middle layer comprising a phosphate buffer containing a calcium ion chelating agent.

4. A reagent as defined in claim 3, wherein the antibody concentration of the antiserum is increased by increasing the antiserum volume.

5. A reagent as defined in claim 3, wherein a selection is made from various antisera provided by various sources so as to obtain the highest antibody concentration sera.

6. A reagent as defined in claim 3, wherein the ratio of antigen to antiserum is made to vary by changing the amount of substrate on which the antigen is adsorbed.

7. A reagent as defined in claim 3, wherein the amount of antigen adsorbed on the substrate is controlled to control said ratio of antigen to antiserum.

8. A reagent as defined in claim 3, wherein said reagent comprises as said antiserum 0.36–0.44 ml of serum taken from rabbits to which were injected HCG, which corresponds to about 7–8 mg of dry extract, and as said substrate 0.36–0.44 ml of a 4% suspension of sheep erythrocytes on which is adsorbed formol-sensibilized HCG, said suspension weighing, after lyophilization, about 16 mg.

9. A reagent in accordance with claim 3 wherein the lower layer comprising said substrate consists essentially of 0.20 to 0.44 ml. of a 3–6% suspension of erythrocytes, which has been lyophilized, having adsorbed thereon said HCG antigen, the top layer which comprises said antiserum consists essentially of 0.30 to 0.60 ml. of dried antiserum, and wherein said chelating agent in said middle layer is ethylenediaminetetraacetic acid present in excess.

* * * * *